United States Patent [19]

Cantarow

[11] Patent Number: 4,824,784

[45] Date of Patent: Apr. 25, 1989

[54] CHROMOGENIC SOLUTION FOR IMMUNOASSAY

[75] Inventor: Walter D. Cantarow, Norwood, Mass.

[73] Assignee: Hygeia Sciences, Incorporated, Newton, Mass.

[21] Appl. No.: 120,182

[22] Filed: Nov. 9, 1987

Related U.S. Application Data

[63] Continuation of Ser. No. 721,102, Apr. 8, 1985, abandoned.

[51] Int. Cl.⁴ .................. G01N 33/53; G01N 33/72; C12Q 1/28; C12N 9/96
[52] U.S. Cl. ........................................... 435/7; 435/28; 435/188; 435/810; 436/66
[58] Field of Search .................. 435/7, 28, 188, 810; 436/531, 66, 18, 518; 422/16; 568/270

[56] References Cited

U.S. PATENT DOCUMENTS

| | | | |
|---|---|---|---|
| 3,791,932 | 2/1974 | Schuurs et al. | 195/103.5 |
| 3,888,629 | 6/1975 | Bagshawe | 23/230 B |
| 4,067,690 | 1/1978 | Cuisia et al. | 422/16 |
| 4,157,280 | 6/1979 | Halbert et al. | 195/127 |
| 4,169,012 | 9/1979 | Dawson et al. | 435/7 |
| 4,248,965 | 2/1981 | Mochida et al. | 435/7 |
| 4,256,833 | 3/1981 | Ali et al. | 435/7 |
| 4,273,868 | 6/1981 | Walter | 435/14 |
| 4,287,300 | 9/1981 | Gibbons et al. | 435/5 |
| 4,299,916 | 11/1981 | Litman et al. | 435/6 |
| 4,340,395 | 7/1982 | Magers et al. | 23/230 B |
| 4,361,648 | 11/1982 | Shuenn-tzong | 435/10 |
| 4,366,241 | 12/1982 | Tom et al. | 435/7 |
| 4,385,114 | 5/1983 | Guthlein et al. | 435/28 |
| 4,386,224 | 5/1983 | Deetman | 568/780 |
| 4,391,904 | 7/1983 | Litman et al. | 435/7 |
| 4,407,943 | 10/1983 | Cole et al. | 435/7 |
| 4,444,879 | 4/1984 | Foster et al. | 435/7 |
| 4,446,232 | 5/1984 | Liotta | 435/7 |
| 4,448,882 | 5/1984 | Brodbeck et al. | 435/188 |
| 4,458,014 | 7/1984 | Ebersole | 435/7 |
| 4,486,530 | 12/1984 | David et al. | 435/7 |
| 4,503,143 | 3/1985 | Gerber et al. | 435/7 |
| 4,525,452 | 6/1985 | Jones et al. | 436/531 |
| 4,540,659 | 9/1985 | Litman et al. | 435/7 |
| 4,615,972 | 10/1986 | Gallacher | 435/28 |
| 4,632,901 | 12/1986 | Valkirs et al. | 435/5 |
| 4,727,019 | 2/1988 | Valkirs et al. | 435/5 |

FOREIGN PATENT DOCUMENTS 8001972 11/1981 Netherlands.
1464359 2/1977 United Kingdom.

OTHER PUBLICATIONS

P. K. Nakane et al., "Peroxidase-Labeled Antibody: A New Method of Conjugation", *J. of Histochemistry and Cytochemistry*, vol. 22, pp. 1084–1091 (1974).

P. Nakane, "Preparation and Standardization of Enzyme-Labeled on Conjugates", *Immunoassays in the Clinical Laboratory*, Alan R. Liss, Inc., pp. 81–87 (1979).

E. Engvall, "Immunochemical Techniques", *Methods in Enzymology*, Part A, H. V. Vunakis et al., eds. Academic Press, pp. 430–432 (1980).

M. Uotila et al., "Two-Site Sandwich Enzyme Immunoassay with Monoclonal Antibodies To Human Alpha Fetoprotein", *J. Immunological Methods*, 42, pp. 11–15 (1981).

E. S. Bos et al., "3,3',5,5'-Tetramethylbenzidine as an Ames Test Negative Chromogen for Horse-Radish Peroxidase In Enzyme-Immunoassay", *J. of Immunoassay*, 2(3&4), pp. 187–204 (1981).

S. Fujita, "Reducing Agents for Quinanes. N,N-Diethylhydroxylamine and Others", *Yuki Gosei Kogaku Kyokaishai*, 37, pp. 960–966 (1979).

*Primary Examiner*—Esther M. Kepplinger
*Assistant Examiner*—Florina B. Hoffer
*Attorney, Agent, or Firm*—John P. Kirby, Jr.; Barry D. Josephs; Margaret A. Pierri

[57] ABSTRACT

A chromogenic solution for enzyme immunoassay. A stabilizing agent is added to chromogenic solutions containing chromogen of the hydrogen donor type. The stabilizing agent is an alkylhydroxylamine, preferably N,N-diethylhydroxylamine. The N-N diethylhydroxylamine retards degradation of the solution of the chromogen in solvent and is particularly effective in retarding discoloration of a chromogen-solvent solution placed in storage over an extended period of time. The alkylhydroxylamine preferably in the form of N,N-diethylhydroxylamine has the additional property that it does not adversely affect the activity of enzymes employed in enzyme immunoassays. It also does not interfere with binding specificity or reactivity of antibodies.

15 Claims, No Drawings

4,824,784

CHROMOGENIC SOLUTION FOR IMMUNOASSAY

This is a continuation, of application Ser. No. 721,102, filed Apr. 8, 1985, entitled CHROMOGENIC SOLUTION FOR IMMUNOASSAY, now abandoned.

BACKGROUND OF THE INVENTION

1. Field of the Invention

This invention relates to biological diagnostic test kits. The invention particularly relates to stabilizers for chromogenic substrates used in enzyme-linked immunosurbent assays.

2. Description of the Background Art

Biological diagnostic test kits, prepackaged assemblages of assay materials, are gaining in popularity, particularly with the advent of the "home" test kit. These kits can be applied to human, veterinary or agricultural testing to detect a wide variety of conditions, commonly by employing antigen specific antibodies, produced in quantity from clones.

Prior to the introduction of test kits, laboratories typically performed these tests using fresh reagents as they were needed. A problem attendant with test kits however, is reagent destabilization as the reagents are left in storage. The mechanism by which destabilization can gradually occur is not well understood. Although gradual environmental oxidation may be a factor, there are likely other contributing factors as yet not understood which may be promoting the destabilization process. The assembled kits may remain on wholesale or retail shelves for extended periods of time, after which they may be stored for even longer periods by the end user. Moreover, storage conditions may often be harmful, for example, under elevated temperatures. These conditions can damage the reagents, rendering test results difficult to interpret, and generally impairing the reliability of the test.

One form of reagent degradation is the discoloration of chromogenic substances to be used in connection with colorimetric enzyme immunoassays. Chromogenic substances particularly those of the hydrogen donor type have a tendency to destabilize when left in storage over long periods of time. This results in a slight color change, typically a yellowig of the chromogenic which occurs gradually over an extended period. Some chromogenic materials, e.g. tetramethylbenzidene; and have been discovered to destabilize less rapidly than others; nonetheless, even this latter chromogen can undergo some discernible yellowing when left in storage for very long periods, particularly under hot environmental conditions. Destabilization of the chromogenic material resulting in yellowing of the chromogen is undesirable, since it can affect the end color change of the chromogen as it reacts to produce a chromophore during conduct of the immunoassay.

Commonly assigned U.S. Pat. No. 4,503,143 discloses an assay which functions as a test kit. The assay is an ELISA test, using tetramethylbenzidine (TMB) as a chromogenic substance. This assay functions quite well, rendering a clearly visible blue color as a positive test result. However, when the kit is stored for very long periods, for example longer than several years and under hot storage conditions, the TMB solution which is normally clear can develop some discernible yellow tinge. The yellow tinge, although slight, poses a potential disadvantage in that it can cause a green tinge to appear in the normally blue chromophore. The green tinge, if pronounced, could possibly be misinterpreted by an inexperienced user.

U.S. Pat. No. 4,067,690 discloses the addition of minute amounts of hydroxylamine to boiler water to retard corrosion due to dissolved oxygen. The hydroxylamine is intended for use in high pressure—high temperature boiler water. The hydroxylamine functions as an oxygen scavenger under these elevated operating conditions to retard corrosion of boiler metal surfaces, generally iron and steel.

U.S. Pat. No. 4,386,224 is directed to use of N,N-diethylhydroxylamine to stabilize color and inhibit color formation in monoalkyl phenols which frequently discolor with age. The hydroxylamine is added in amounts ranging from about 5 parts per million to about 50 parts per million of the alkyl phenol. This reference also discloses that the N,N-diethylhydroxylamine can reduce the color of monoalkyl phenols in which color development has taken place.

Accordingly, it is an object of the invention to retard degradation and discoloration of a chromogen during storage.

It is an object of the invention to provide a stabilizing agent for the chromogenic solutions to be used in enzyme immunoassays wherein the stabilizing agent retards discoloration of the chromogenic solution over an extended period of time in excess of one year.

It is a further object to provide a stabilizing agent to retard discoloration of chromogenic solutions of the hydrogen donor type to be used in colorimetric enzyme immunoassay kits.

SUMMARY OF THE INVENTION

In accomplishing the foregoing and related objects, the invention provides a diagnostic test kit comprising antibody-enzyme complexes, a chromogen, and a chromogen stabilizing agent, and an oxidizing agent for the chromogen responsive to the enzyme.

In accordance with one aspect of the invention, the chromogen is tetramethylbenzidine. This chromogen is oxidized in an enzymatically induced reaction with hydrogen peroxide to form a chromophore exhibiting a visually distinct blue color.

In accordance with another aspect of the invention, a chromogen stabilizing agent is added to prevent destabilization of the chromogen in solvent during extended storage periods, or when the chromogen-solvent solution is stored under elevated temperatures. An effective amount of an alkylhydroxylamine is added to the chromogen solution in the range of 1:50,000 to 1:500,000 parts by volume, preferably 1:50,000 to 1:200,000 parts by volume, which prevents chromogen degradation. N,N-diethylhydroxylamine (DHA) for example, has been found to be a particularly effective compund, which is soluble in the chromogen-solvent solution. It has also been determined that the addition of N,N-diethylhydroxylamine to the solution of chromogen and solvent will quickly reverse any yellowing discernible therein to result in a near colorless chromogenic solution.

A principle advantage discovered in the use of an alkylhydroxylamine as stabilizing agent for the chromogenic solution is that the alkylhydroxylamine does not adversely affect the reactivity of immunoassay components with which the chromogenic solution will ultimately come into contact. Specifically, the alkylhydroxylamine in above stated concentration has been found not to adversely affect the reactivity of enzymes, for example peroxidase typically employed in enzyme linked immunosorbent assays or the binding properties of antibodies and antigens employed in such assays. Additionally, the alkylhydroxylamine in the above stated concentration does not inhibit the oxidizing properties of peroxides e.g. hydrogen peroxide, which are normally added to the chromogenic solution as oxidizing agent in order to activate the chromogenic solution just prior to use in the assay.

The alkylhydroxylamine, preferably N,N-diethylhydroxylamine when added to the chromogenic solution has been discovered to stabilize the chromogen permitting the chromogen to be stored for at least one year, typically at least several year's duration without noticeable yellowing of the chromogenic solution occuring during the storage period.

This desirable result is realized when chromogens of the hydrogen donor type, particularly tetramethylbenzidine are employed. The preferred concentration of the N,N-diethylhyroxylamine in a chromogenic-solvent solution wherein the chromogen is a tetramethylbenzidine has been determined to be in a range between about 1 part by volume N,N-diethylhydroxylamine to 50,000 parts by volume chromogen-solvent solution up to about 1 part N,N-diethylhydroxylamine to 200,000 parts chromogen-solvent solution.

A more preferred concentration wherein the chromogen is a tetramethylbenzidine has been determined to be in a range between about 1 part N,N-diethylhydroxylamine to 100,000 parts chromogen-solvent solution to 1 part N,N-diethylhydroxylamine to 200,000 parts chromogen-solvent solution.

DETAILED DESCRIPTION

In accordance with the invention, an enzyme immunoassay procedure and testing kit is provided utilizing antibody-enzyme complexes a chromogenic substrate responsive to the enzyme, and a chromogen stabilizing agent. The chromogen stabilizing agent serves to prevent undesirable degradation manifested by discoloration of chromogen without interfering with the reactivity of the enzyme or binding specificity and avidity of the antibodies. The stabilizing agent of the present invention is particularly applicable to colorimetric enzyme immunosassays to be provided in the form of a diagnostic testing kit. The stabilizing agent of the invention has preferred application to chromogenic solutions containing chromogens of the hydrogen donor type for example 0-phenylenediamine (OPD), O-tolidine and particularly tetramethylbenzidine. A typical application of the stabilizing agent is as an additive to a chromogenic solution to be included as a component of an enzyme linked immunosorbent assay diagnostic test kit.

Typical chromogenic substrates employed in colormetric enzyme immunoassay to which the present invention applies are chromogens of the hydrogen donor type. A particularly advantageous chromogen is tetramethylbenzidene. When TMB chromogen is employed in an enzyme immunoassay, it oxidizes in the presence of an enzyme, typically a peroxidase, and a peroxide oxidizing agent. The resulting product is a chromophore having an easily discernible blue color. This indicates the presence of test antigen being assayed, since the antigen becomes linked to an antibody-enzyme complex of the immunoassay. To prevent visible degradation, i.e. discoloration of the TMB during prolonged storage of the test kit, the invention provides for the inclusion of a stabilizing agent in the form of an alkylhydroxylamine. The alkylhydroxylamine is added to the chromogenic solution which typically contains a chromogen and solvent. The chromogenic solution with alkylhydroxylamine included therein is kept as a separate component of the test kit until time for conduct of the assay. The stabilizing agent of the invention has been determined to play an important role in colorimetric enzyme immunoassay test kits wherein storage durations have been prolonged or environmental conditions harsh, causing some visible discoloration of the chromogen prior to use.

A preferred stabilizing agent for the chromogen which has been discovered to be particularly advantageous is N,N-diethylhydroxylamine. This alkylhydroxylamine is a particularly effective stabilizing agent for tetramethylbenzidine (TMB). It has been discovered that minute addition of N,N-diethylhydroxylamine to TMB chromogenic solutions retards the rate of discoloration so significantly that yellowing of the chromogenic solution is either imperceptible to the naked eye or barely perceptible even after the chromogenic solution is left in storage over one year's time and subjected to elevated environmental temperatures during this period.

The N,N-diethylhydroxylamine has been determined to be a particularly advantageous stabilizing agent for tetramethylbenzidine, since it does not adversely affect the reactivity of an oxidoreductase enzyme, typically a peroxidase, employed in the assay. It also does not interfere with binding specificity or avidity of the antibodies employed in the assay and does not interfere with the oxidation of the chromogen to chromophore by the admixture of peroxide into the chromogenic-solvent solution at time of use. Common biochemical antioxidants for example sulfur containing antioxidants have been found to be unsuitable in the present application, since they do not retard yellowing of chromogen without also adversely affecting the reactivity of the other assay reagents.

An effective concentration range of the N,N-diethylhydroxylamine (DHA) in the chromogen solution which accomplishes the foregoing results has been determined to be in a range between about 1 part by volume DHA to 50,000 parts by volume chromogen-solvent solution up to about 1 part by volume DHA to 200,000 parts chromogen-solvent solution.

A preferred formulation for an activated tetramethylbenzidene chromogenic solution with the preferred stabilizing agent of the invention added thereto is illustrated in Example 1: The following examples incorporates subject matter from commonly assigned U.S. Pat. No. 4,503,143 herein incorporated by reference (U.S. No. 4,503,143 makes no mention of use of an alkylhydroxylamine additive.)

EXAMPLE 1

The following mixure, exclusive of the use of N,N-diethylhydroxylamine additive, appears in commonly assigned U.S. Pat. No. 4503143 herein incorporated by reference. An activated TMB chromogenic solution was prepared by mixing 4.0 parts by volume of reagent (i) with 11.0 parts by volume of reagent (ii), and then adding 0.010 part by volume of the 30 percent hydrogen peroxide solution (reagent (iii)). The mixture was stirred to form a homogeneous, activated TMB solution. The individual reagents were produced as follows:

Reagent(i)

Reagent (i) was prepared by dissolving 1.25 g (5.20 mMol) of 3,3,',5,5'-tetramethylbenzidine, in 1.00 liter absolute methanol with or without heating. Diethylhydroxylamine was added to the TMB/solvent solution to a concentration of 1 part by volume N,N-diethylhydroxylamine to 100,000 parts by volume of the TMB/solvent solution. A clear colorless or faintly tan solution resulted which could be stored for at least 1 year at 4 to 25 C, in a brown bottle without affecting its usefulness in an enzyme immunoassay.

Reagent (ii)

Reagent (ii) is a buffer prepared by first dissolving 144.8 grams (1.020 mol) of disodium hydrogen phosphate in 1.00 liter hot deionized water. The phosphate dissolved in the hot deionized water upon stirring. To this solution 102.95 grams (0.4902 mol) of citric acid monohydrate were added. The resulting solution was then diluted to 10.0 liters with additional deionized water, thus forming a citrate-phosphate solution, with a pH of 5.0.

Reagent(iii)

Reagent(iii) consisted of an aqueous solution of hydrogen peroxide, wherein the hydrogen peroxide comprised 30 percent by volume.

Applications of the improved chromogenic solution employing N,N-diethylhydroxylamine additive for use in preferred enzyme imunoassay are illustrated in the following examples.

EXAMPLE TWO

The following protocol is not limited to specific types of antigen; however, it has been found particularly suitable as a double sandwich enzyme immunoassay for human luteinizing hormone (HLH) and human chorionic gonadotropin hormone (HCG). The procedure involved coating the support plate with a first antibody, adding the antigen sample, and then a second antibody-enzyme conjugate. The first and second antibodies in the various assays were obtained from monoclonal hybridoma antibodies prepared from inoculated mice or polyclonal antisera generated by the inoculation of rabbits with the test antigen. The antisera were purified by successive precipitations with ammonium sulfate.

Wells of a polystyrene microliter plate were coated with the first antibody: a coating antibody solution was added to each well, and this was incubated for 1–4 hours at room temperature, then decanted. Three hundred microliters of a PBS/0.5% BSA blocking solution (0.5 gm bovine serum albumin per 100 ml of phosphate buffered saline) were added to the wells and incubated for thirty minutes. The wells were then decanted and twice washed with PBS/Tween buffer. The PBS/Tween buffer was composed of 0.1 vol. percent Tween Solution and 99.9 vol. percent PBS.

A solution to be tested for antigen was added to the wells and incubated. The incubation times were thirty minutes for HCG and one hour for HLH. The wells were then decanted and washed with PBS/Tween buffer.

A solution of horseradish peroxide-conjugated second antibody, which may typically be conjugated with glutaraldehyde or avidin-biotin was added to the wells, and incubated for thirty minutes at room temperature. After decanting and washing with PBS/Tween buffer, 150 microliters of the TMB activated solution of Example 1 were added.

The activated chromogen solution was made in accordance with Example 1, by mixing 4.0 parts by volume of reagent (i) with 11.0 parts by volume of reagent (ii), and then adding 0.010 part by volume of the 30 percent hydrogen peroxide solution (reagent iii). The mixture was stirred to form a homogeneous, activated TMB solution which contained N,N-diethylhydroxylamine in the concentration specified in Example 1. The chromogen-containing solution was allowed to incubate for between 5 and 30 minutes at room temperature. Then an absorbance reading was taken at 660 nanometers (nm) using a Dynatech Microlisa MR 580 Autoreader, available from Dynatech Laboratories, Alexandria, Virginia. The protocol set forth in Example 2 was used successfully to detect HCG hormone at concentrations as low as 7.8 nanograms/ml. and HLH at concentrations as low as 7.8 nangorams/ml.

The rate of color development, as measured by change in absorbance of the activated TMB solution at wavelength of maximum absorbance, 660 nm, was at least three times greater than that achieved with the use of the chromogen o-phenylenediamine (OPD) dissolved in its optimun hydrogen peroxide concentration. The absorbance of OPD color change was also measured at its wavelength of maximum absorbance.)

EXAMPLE 3

The double-antibody sandwich ELISA assay of Example 2 was repeated for HCG with the following modifications: The antigen solution and enzyme-conjugated second antibody were added and incubated essentially simultaneously in the wells coated with the first antibody. Specifically the antigen solution and enzyme-conjugate were first admixed and essentially immediately thereafter the mixture was added to the wells coated with first antibody. The mixture was incubated in the antibody-coated wells for a period of thirty minutes at room temperature. This abbreviated assay provided results comparable to those of Example 2, and resulted in at least three times faster color development than would occur if OPD chromogen were used in this same assay under optimal hydrogen peroxide concentration. The protocol set forth in Example 3 was used successfully to detect HCG hormone at concentrations as low as 7.8 nanograms/ml. (urine).

EXAMPLE 4

The assay methods set forth in the above general description and illustrative examples may be applied in a home diagnostic assay kit. For example, a number of vials containing the various immunologic reagents required for the assay may be included in such a kit. The user need then only mix these reagents with the test sample in accordance with a given protocol and await a color change in the final solution. One method of application of the double antibody sandwich ELISA to a home diagnostic kit could be effected, illustratively, by providing the kit with one vial (vial 1), which has been precoated with a first antibody and blocking solution and a second vial (vial 2) which would contain the second antibody—enzyme conjugated preferably in lyophilized form. A third vial (vial 3) could contain a solution of the chromogen and solvent, and a vial 4 could contain the solution of buffer and hydrogen peroxide.

In the carrying out the assay, the user need only collect a sample (for example a urine specimen) suspected of containing the antigen to which the assay is directed. The user might take a sample of the urine with a dropper supplied in the kit and may add a few droplets to vial 2. The contents of vial 2 would be immediately transferred to vial 1 and the solution therein allowed to incubate for a prescribed period at room temperature. The user could thereupon discard the liquid contents of vial 1 and rinse the vial several times with cold tap water. The contents of vial 4 could then be mixed with those of vial 3 to form an activated chromogenic solution in vial 3. The user could then transfer this solution to vial 1, wait another prescribed period of time, and then observe whether the contents of vial 1 have developed color, thus determining the presence of the antigen being assayed.

These assays described herein are advantageously implemented using room temperature incubations. They have been successfully conducted at temperatures in the range 15° C. to less than about 37° C. for all steps in the assay including the incubation of first antibody to effect adsorption of this antibody to a solid surface. The preferred temperature range for all steps in the assay is 15° C.-28° C.

Although the enzyme immunoassay techniques of the invention have been illustrated in the foregoing detailed description in the context of certain specific enzyme linked immunosorbent assays, it should be appreciated that they may be extended to a variety of enzyme immunoassays. Accordingly, the invention is not intended to be limited to the specific embodiments or examples set forth in the specification, but rather is defined by the claims and equivalents thereof.

What is claimed is:

1. In an enzyme immunoassay for the colorimetric detection of an antigen comprising the steps of adsorbing a quantity of a first antibody to a solid support; forming a conjugate between an immunologic reagent and an oxidoreductase enzyme; mixing said conjugate with a sample to be tested for an antigen so that said antigen binds to said first antibody and to said conjugate to form an immunologic complex in solid phase; determining the presence of said enzyme in the adsorbed material by subjecting the adsorbed material to a chromogenic substrate comprising a chromogen which is a hydrogen donor; and monitoring the visible color characteristics of said substrate; the improvement comprising that said chromogenic substrate is provided in a chromogenic solution comprising a chromogen, a solvent and a stabilizing agent comprising an alkylhydroxylamine which is soluble in the chromogenic solution and which functions to retard discoloration of the chromogen during storage of the chromogenic substrate prior to use in said assay, said stabilizing agent being present in an amount sufficient to stabilize said chromogen and having the additional properties that it does not adversely affect either the reactivity of the enzyme or the binding specificity and avidity of the first antibody and said conjugate for said antigen.

2. An enzyme immunoassay as in claim 1 wherein the stabilizing agent is N,N-diethylhydroxylamine.

3. An enzyme immunoassay as in claim 2 wherein said N,N-diethylhydroxylamine is present in said solution at a concentration in a range between about 1 part N,N-diethylhydroxylamine to 50,000 parts solution up to about 1 part N,N-diethylhydroxylamine to 200,000 parts solution.

4. An enzyme immunoassay as in claim 1 wherein the chromogen is a tetramethylbenzidine.

5. An enzyme immunoassay as in claim 1 wherein the enzyme is a peroxidase.

6. A diagnostic kit for carrying out an enzyme linked immunosorbent assay for detection of an antigen wherein said kit is suitable for home diagnostic and clinical application and is to be employed and stored under ambient room temperature conditions, said kit comprising (a) a solid support precoated with a first antibody; (b) a solution comprising a conjugate of an oxidoreduclase enzyme with a second antibody; and (c) a separately contained chromogenic solution responsive to an oxidoreduclase enzyme for said immunosorbent assay, said chromogenic solution comprising a chromogenic substrate having the properties of a hydrogen donor; wherein the improvement comprises that said chromogenic substrate is in the presence of a stabilizing agent comprising an alkylhydroxylamine functioning to retard discoloration of the chromogen during storage of the chromogenic substrate prior to use in said assay, said alkylhydroxylamine having the properties that it is soluble in the chromogenic solution, that it does not adversely affect either the reactivity of the enzyme or the binding specificity and avidity of any immunologic reagent for said antigen.

7. A diagnostic kit as in claim 6 wherein the stabilizing agent is N,N-diethylhydroxylamine.

8. A diagnostic kit as in claim 7 wherein the chromogenic substrate is provided in a chromogenic solution comprising a chromogen and solvent and the N,N-diethylhdroxylamine in said solution has a concentration in a range between about 1 part N,N-diethylhdroxylamine to 50,000 parts solution up to about 1 part N,N-diethylhdroxylamine to 200,000 parts solution.

9. A diagnostic kit as in claim 6 wherein the chromogen is a tetramethylbenzidine.

10. A diagnostic kit as in claim 6 wherein the enzyme is a peroxidase.

11. A chromogenic solution for use in an enzyme immunoassay comprising a chromogenic substrate having properties of a hydrogen donor, and a solvent, said chromogenic solution being capable of reacting with a peroxide in the presence of said enzyme in said immunoassay to produce a chromophore having visible color characteristics, wherein the improvement comprises the presence in said chromogenic solution of a stabilizing agent comprising an alkylhydroxylamine which is soluble in the chromogenic solution and which functions to retard discoloration of the chromogenic solution during storage prior to use in said immunoassay, said stabilizing agent having the additional properties that it does not adversely affect either the reactivity of the enzyme or the binding specificity and avidity of immunologic reagents in said immunoassay.

12. A chromogenic solution as in claim 11 wherein the stabilizing agent is N,N-diethylhydroxylamine.

13. A chromogenic solution as in claim 12 wherein the N,N-diethylhydroxylamine in said solution has a concentration in a range between about 1 part N-N diethylhydroxylamine to 50,000 parts solution up to about 1 part N-N diethylhydroxylamine to 200,000 parts solution.

14. A chromogenic solution as in claim 11 wherein the chromogenic substance is a tetramethylbenzidine.

15. A chromogenic solution as in claim 11 wherein the enzyme is a peroxidase.

* * * * *